United States Patent [19]
Fitzgibbons, Jr.

[11] Patent Number: 5,476,470
[45] Date of Patent: Dec. 19, 1995

[54] TROCAR SITE SUTURING DEVICE

[76] Inventor: Robert J. Fitzgibbons, Jr., 115 S. 128 Plz., Omaha, Nebr. 68154

[21] Appl. No.: 228,792

[22] Filed: Apr. 15, 1994

[51] Int. Cl.⁶ ................................. A61B 17/04
[52] U.S. Cl. ................ 606/144; 606/139; 606/148
[58] Field of Search ................ 606/139, 144–148, 606/184–187; 112/80.03, 169

[56] References Cited

U.S. PATENT DOCUMENTS

| | | | |
|---|---|---|---|
| 5,304,184 | 4/1994 | Hathaway et al. | 606/144 |
| 5,364,408 | 11/1994 | Gordon | 606/144 |
| 5,368,601 | 11/1994 | Sauer et al. | 606/139 |
| 5,403,329 | 4/1995 | Hinchcliffe | 606/144 |

*Primary Examiner*—Gary Jackson
*Attorney, Agent, or Firm*—Henderson & Sturm

[57] ABSTRACT

A device for suturing closed laparoscopic trocar sites to reduce the incidence of incisional herniation. A pair of needles, hollow and having an eyelet adjacent the pointed end, are secured to a clip which may be fastened over a trocar sheath. The clip is then forced to slide down the sheath and the two needles penetrate the fascia and underlying muscle surrounding the hole formed by the trocar. The needles may also be spread somewhat after passing within the skin in to gain a better bite on the tissue surrounding the trocar sheath. A suture is then threaded down through one hollow needle and passed through the eyelet of the second needle, utilizing the laparoscope and a second accessory sheath. When the device is then withdrawn, the suture remains, passing through the peritoneum, muscle and fascia and may be tightened to close the site upon removal of the sheath.

7 Claims, 7 Drawing Sheets

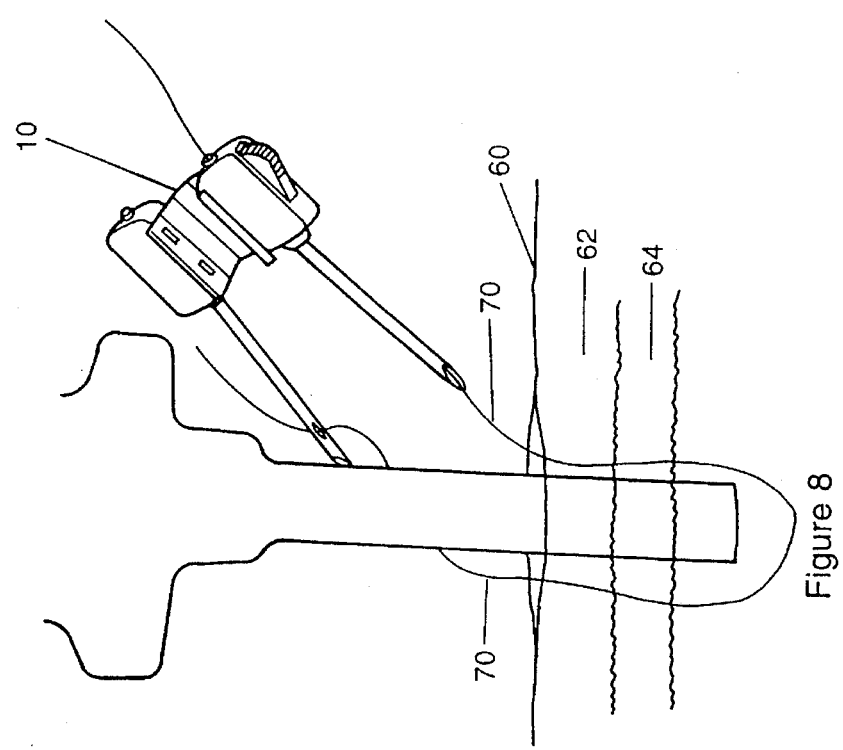
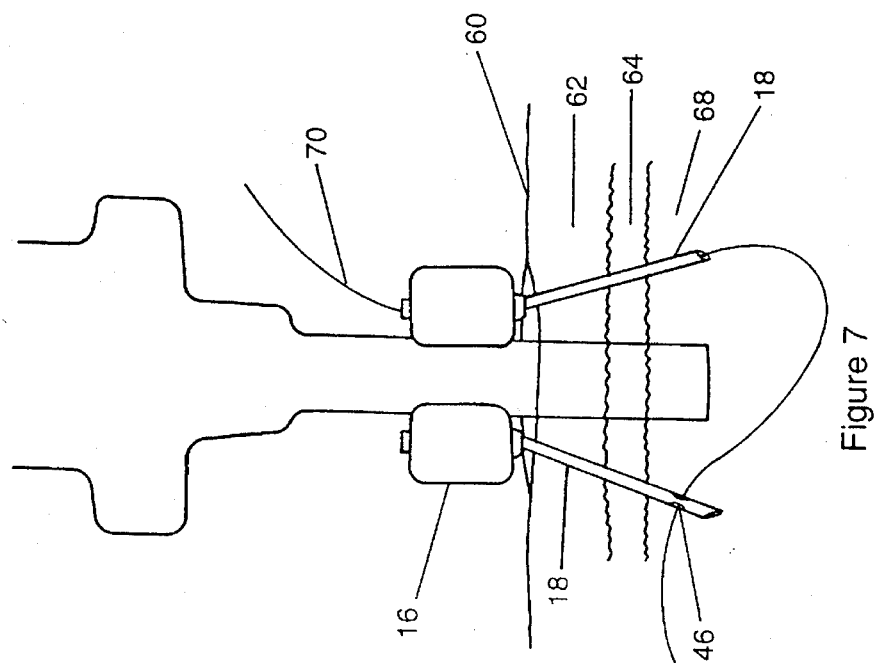

TROCAR SITE SUTURING DEVICE

TECHNICAL FIELD

The present invention relates to surgical suturing devices, and more particularly to a device for suturing closed trocar entrance sites.

BACKGROUND ART

Laparoscopic surgery is a means of performing diagnostic and therapeutic procedures after first gaining entrance to the abdominal cavity, and involves the visual examination of the cavity by means of a laparoscope. Although reports of laparoscopic surgery were first published early in the 20th century, the use of this technique was confined to diagnosis of abdominal pain and ligation of the fallopian tubes until recently when development of miniature video cameras permitted "televising" the operative field.

Laparoscopic surgery involves creating a working space within the abdominal cavity by insufflating the peritoneal cavity with carbon dioxide. The laparoscope is then inserted into the abdomen with a trocar and hollow sheath containing a side port for continuous carbon dioxide insufflation. The sheath also contains valves and gaskets to allow the insertion and removal of the laparoscope without allowing the carbon dioxide to escape. For an operation, accessory sheaths are inserted to introduce laparoscopic instruments. These instruments are generally elongated, narrower versions of standard surgical tools. The surgeon works with instruments inserted through one or two sheaths while the laparoscope is focused on the operative field by an assistant. The video cameras have a high resolution and, when attached to the laparoscopic eyepiece, magnify images 5 to 15 times and provide a clear image of the operative field.

DISCLOSURE OF THE INVENTION

One difficulty which has developed from current laparoscopic surgical techniques is the incidence of incisional herniation at the Trocar sites. These occasionally develop because the muscle and fascia which are penetrated during the procedure is not sutured closed. The present invention discloses a device for suturing closed the muscle and fascia at trocar sites. A pair of needles, each hollow and having an eyelet adjacent its pointed end, are secured to a clip which may be fastened over a trocar sheath. The clip is then forced to slide down the sheath and the two needles penetrate the fascia and underlying muscle surrounding the incision formed by the trocar. A suture is then threaded down through one needle and passed through the eyelet of the second needle, utilizing the laparoscope and a second accessory sheath. When the device is then withdrawn, the suture remains, passing through the muscle and fascia, and may be tightened to close the site upon removal of the trocar sheath.

BRIEF DESCRIPTION OF THE DRAWINGS

These and other attributes of the invention will become more clear upon a thorough study of the following description of the best mode for carrying out the invention, particularly when reviewed in conjunction with the drawings, wherein:

FIG. 7 is a sectional view depicting the threading of the needles after passing into the abdominal cavity;

FIG. 8 is a cross-sectional view with the invention withdrawn from the abdomen, but with the trocar sheath still in place.

BEST MODE FOR CARRYING OUT THE INVENTION

Figure 1:
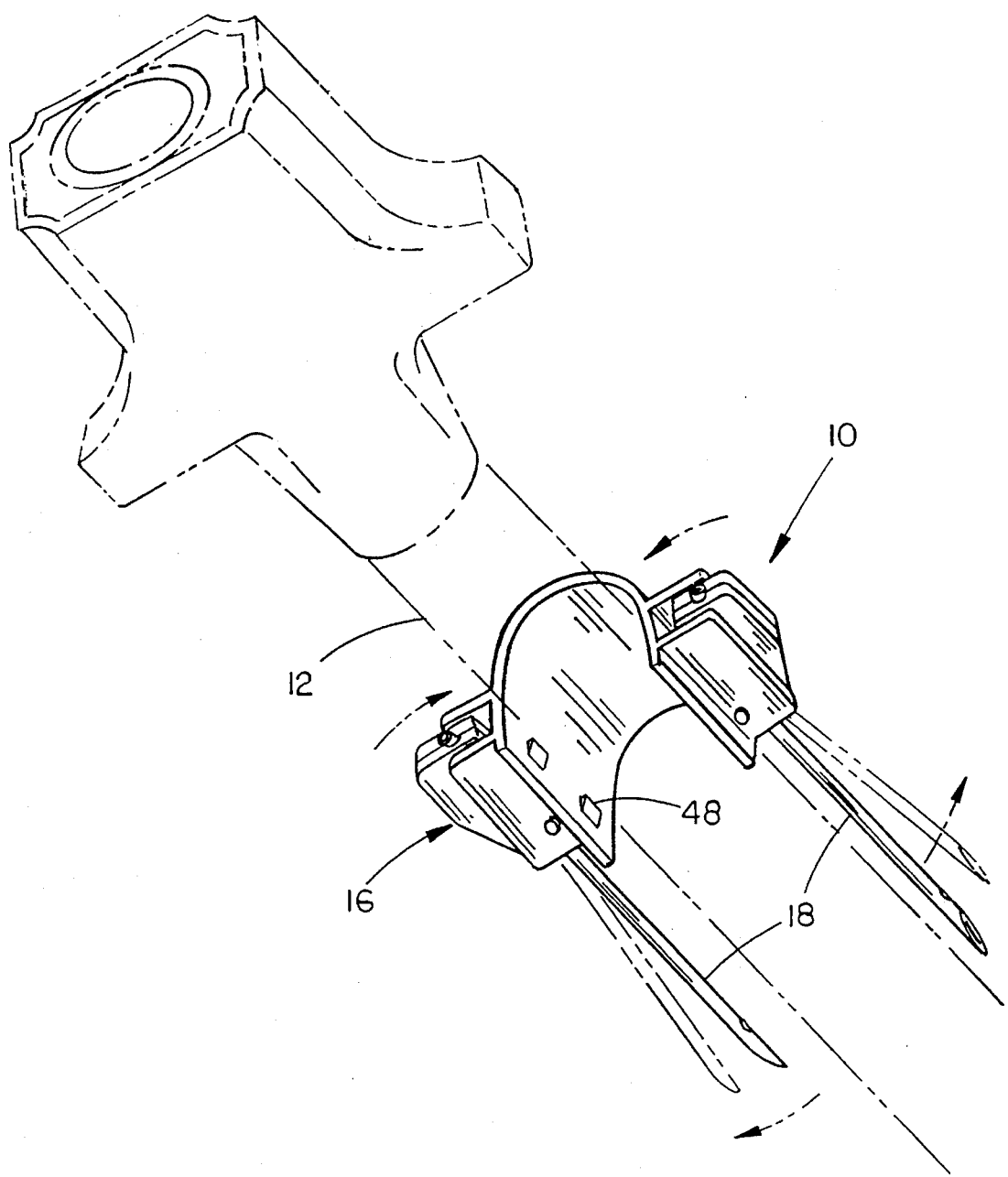
FIG. 1 is a perspective view of the invention, shown attached to a trocar sheath depicted in dashed lines.
Figure 2:
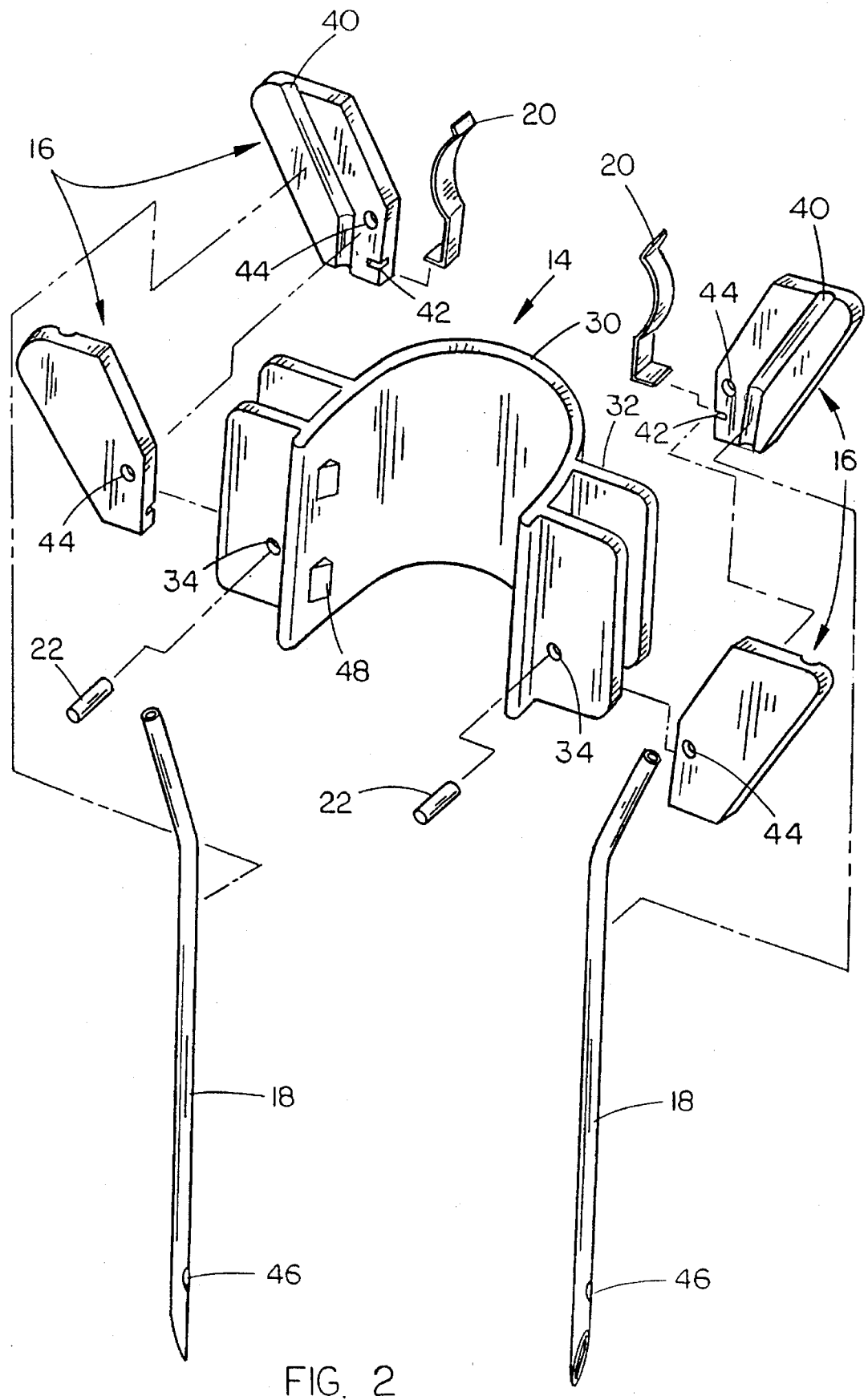
FIG. 2 is an exploded view of the invention.
Figure 3:
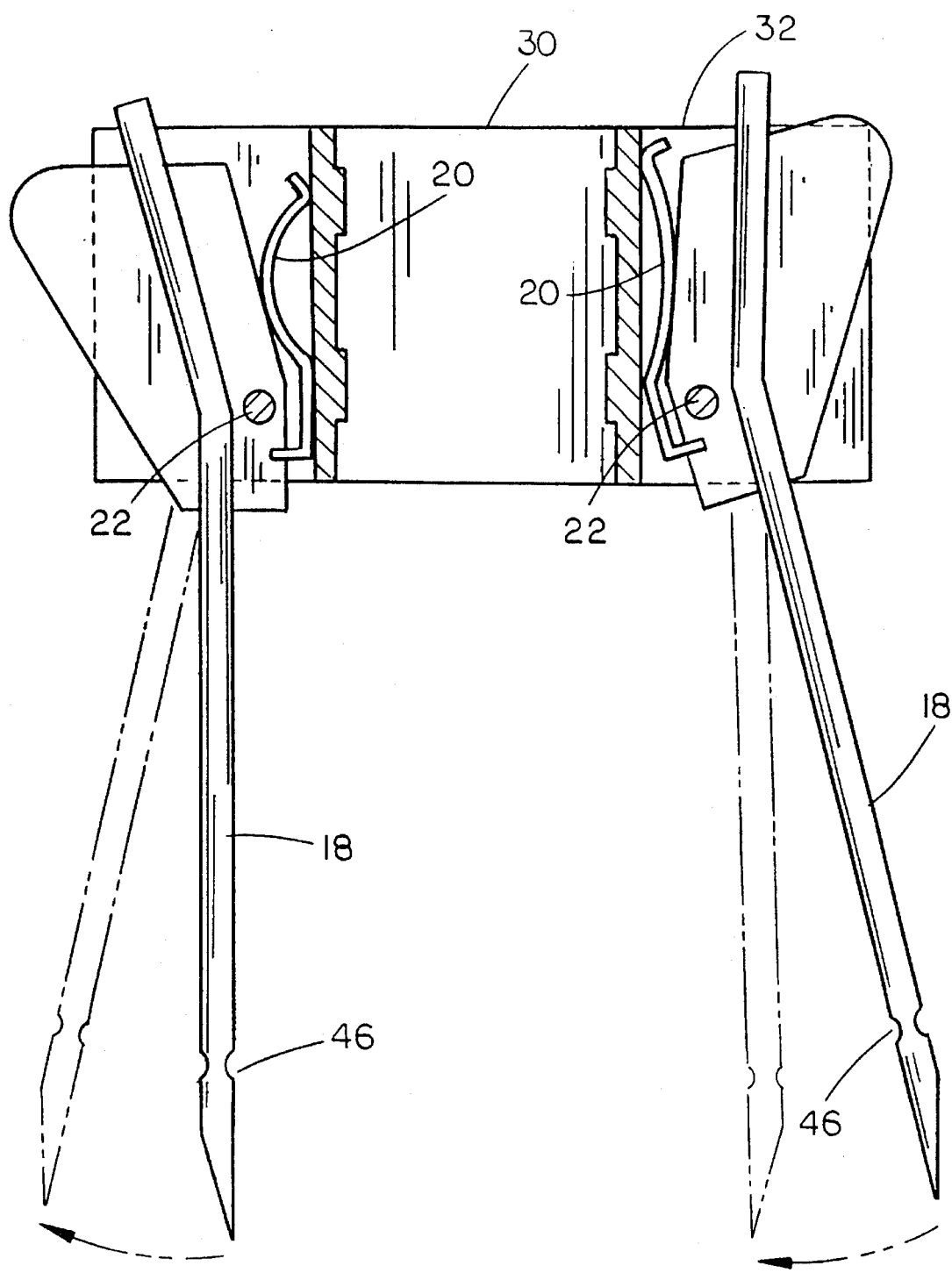
FIG. 3 is a cross-sectional view of the invention.

Referring now to the drawings, wherein like reference numerals designate identical or corresponding parts throughout the several views, FIG. 1 shows a trocar site suturing device 10, constructed in accordance with the present invention, which has been placed over a trocar sheath 12 in preparation for use. As is best seen in FIG. 2 and FIG. 3, the invention 10 includes a support clip 14, a pair of pivot blocks 16, two hollow needles 18, a spring 20 for each of the pivot blocks 16, and a pivot pin 22 for each of the pivot blocks 16. While the needles 18 are preferably made of stainless steel, the remaining components of the invention may be made of stainless steel or of plastic or other similar material, depending on whether or not the device is to be sterilized for reuse or disposed of after each use.

The support clip 14 is comprised of a semi-circular ring 30 which carries a pair of brackets 32 on opposing sides of the ring 30 adjacent the ring opening. The brackets 32 have an aperture 34 passing therethrough for receiving a pivot pin 22, as will be further described below. The semi-circular ring 30 also carries at least two, and preferably four small protrusions 48 axially aligned with the ring 30 adjacent the ring opening which function to snap over the trocar sheath 12 and hold the invention 10 in place on the sheath. An alternate embodiment of the invention could instead utilize a ring 30 slightly more than semi-circular in shape, wherein the ring opening itself would snap over the trocar sheath 12.

The pivot blocks 16 are formed from two separate mirror image pieces having a somewhat triangular shape, each of which carries a semi-circular groove 40 formed into the interior surface as can be clearly seen in FIG. 2. In the lower portion of the pivot block 16, the semi-circular groove 40 forms an abrupt angle of approximately 10 degrees, to accommodate the needles 18 having a similar shape. The needle 18 is thus fitted into the grooves 40 and sandwiched between the two pivot block 16 halves as they are secured together as by glue or welding, thereby securing the needles 18 therein. The pivot blocks 16 also have a small aperture 42 formed therein for receiving one end of a small leaf spring 20. This serves to position the leaf spring 20 between the pivot block 16 and the side of the ring 30 when the pivot block 16 is positioned into the bracket 32 and the pivot pin 22 is inserted through the pivot pin hole 34 and a pivot pin hole 44 passing through the pivot block 16. The spring 20 thus functions to bias the top of the pivot block 16 outward and the lower portion of the pivot block 16 inward. This biasing thus pivots the sharp end of the needles 18 inward such that they are essentially parallel with each other and are held adjacent the trocar sheath 12 when the invention is readied for use.

The gauge of the needles 18 may range from approximately 12 to 18, and may range from one to four inches in length, depending on the thickness of the abdominal wall of the patient. Each of the needles 18 is hollow and has a small aperture or eyelet 46 formed through the needle 18 adjacent the sharp end.

It may therefore be understood that, when the invention 10 is snapped onto a trocar sheath 12 as seen in FIG. 1, the two needles 18 will be held adjacent the trocar sheath due to the biasing of the springs 20. This biasing is easily overcome by squeezing the two pivot blocks 16 inward, causing the pivot blocks 16 to pivot on pivot pin 22. This pivoting action causes the pointed ends of the needles 18 to rotate outward, away from the trocar sheath 12 at approximately a 10 degree angle.

Figure 4:
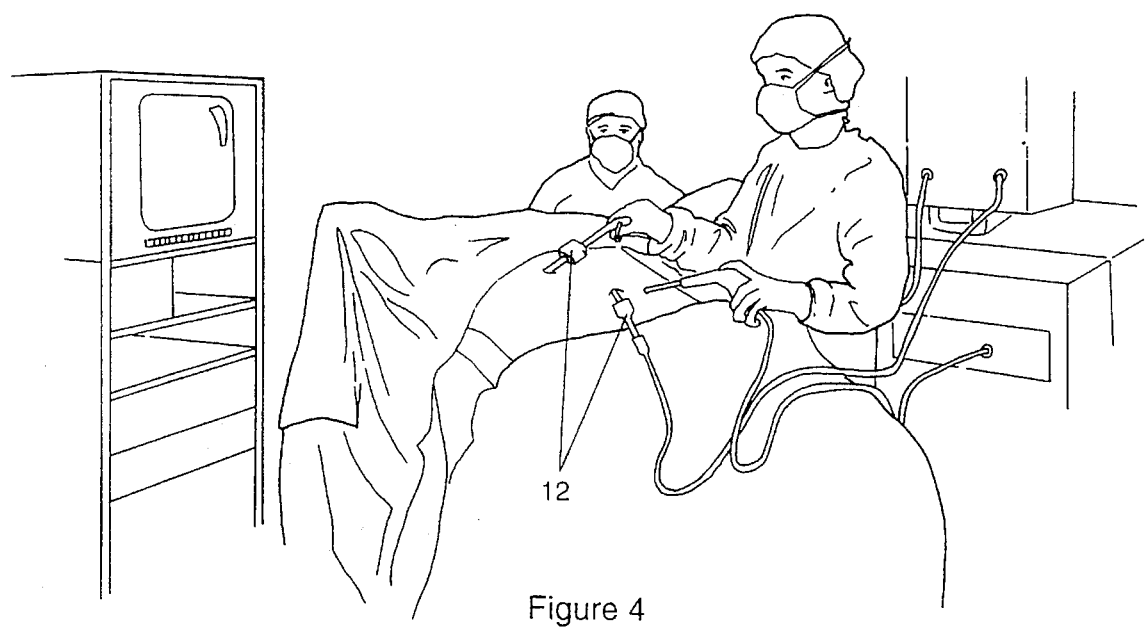
FIG. 4 depicts a typical laparoscopic surgical procedure.
Figure 6:
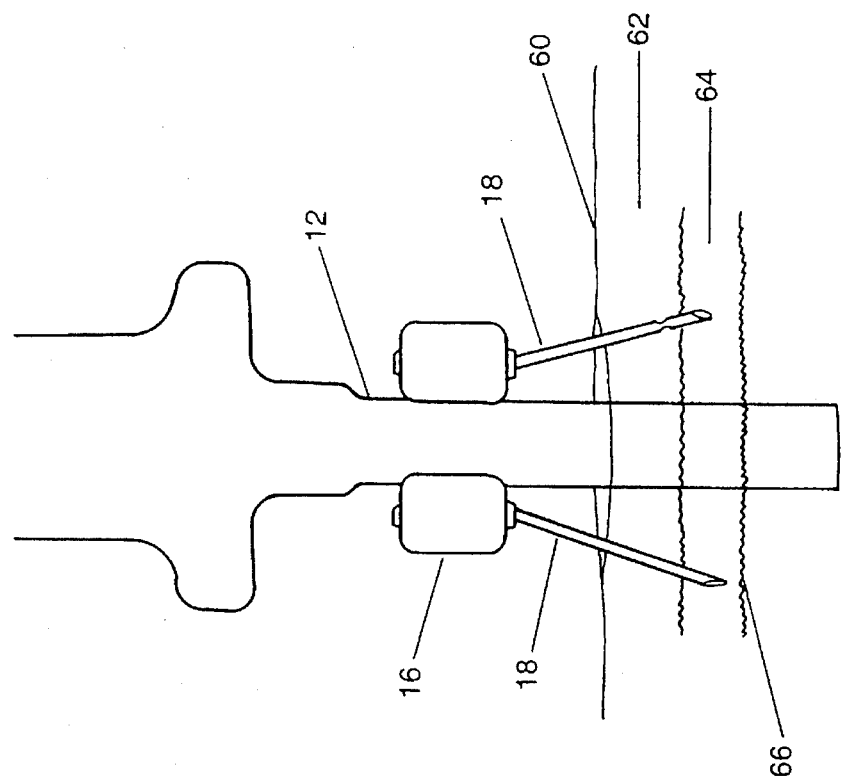
FIG. 6 is a sectional view depicting the suturing procedure after the needles have been extended.
Figure 5:
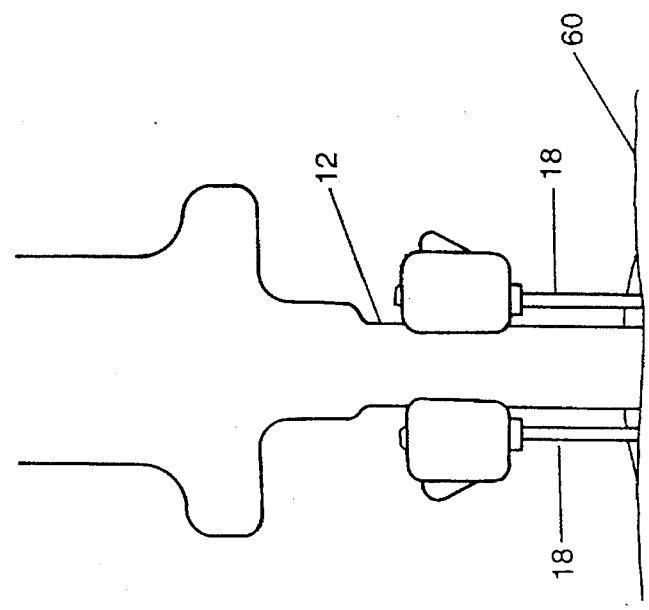
FIG. 5 is a perspective view showing the placement of the invention at the beginning of the suturing procedure.
Figure 9:
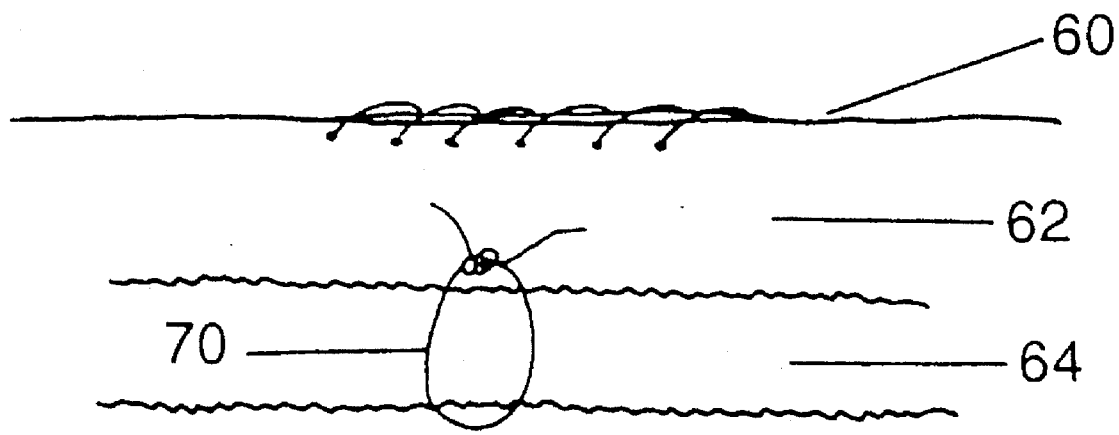
FIG. 9 is a sectional view depicting the tied off suture closing the trocar site incision through the fascia, muscle and peritoneum.

Referring now to FIGS. 4 through 9, the use of the invention will be explained. FIG. 4 depicts several trocar sheaths 12 extending to within a surgical patient's abdominal cavity as is common for laparoscopic surgery. When the surgical procedure is complete, the trocar sites will be sutured closed utilizing the present invention, thereby preventing incisional herniation. FIG. 5 depicts the first step wherein the invention is snapped onto a trocar sheath 12 and the invention is forced to slide downward along the sheath until the needles 18 pass within an incision made through the skin 60. As seen in FIG. 6, the needles 18 penetrate into the fat layer 62 and are then pivoted into an extended position by squeezing the two pivot blocks 16 toward the sheath 12. This action moves the needles 18 away from the trocar sheath 12 and positions the needles to penetrate the underlying muscle 64 and peritoneum 66 with sufficient "bite" to prevent the sutures from tearing out. FIG. 7 depicts the invention as the needles have penetrated into the abdominal cavity 68. A suture 70 is then threaded down through one of the hollow needles 18 and passed through the eyelet 46 of the opposing needle 18, this being accomplished utilizing the laparoscope and laparoscopic instruments of opposing trocar sheaths. Next, as seen in FIG. 8, the invention 10 is withdrawn, and in so doing the suture 70 is readied for tightening and tying off as depicted in FIG. 9. The incision in the skin is then closed in the standard manner. It should be understood that the sutures may be placed around each trocar site while the trocar sheath remains in place, thus allowing all of the sites to be sutured closed. The final site to be closed will normally be the site through which the laparoscope is originally inserted. That is, all other sites will receive sutures, then the laparoscope will be moved to one of these sites and the original laparoscope site will receive the final suture. Then all trocar sheaths may be removed and all sites closed.

While the invention has been described with a certain degree of particularity, it is manifest that many changes may be made in the details of construction and the arrangement of the components without departing from the spirit and scope of the disclosure. It is therefore to be understood that the invention is not limited to the embodiment set forth herein for purposes of exemplification, but is to be limited only by the scope of the appended claims, including the full range of equivalency to which each element thereof is entitled.

What is claimed is:

1. A device for suturing trocar sites closed, comprising:
   (a) a first needle and a second needle, each having a pointed end and a non-pointed end, said first needle being hollow, said second needle having an eyelet passing therethrough adjacent said pointed end; and
   (b) means for receiving said needles and slidably mounting said needles in a parallel, spaced apart relation on a trocar sheath.

2. The device for suturing trocar sites as recited in claim 1 wherein said mounting means comprises a substantially semi-circular ring.

3. The device for suturing trocar sites as recited in claim 2 wherein said needles are affixed on opposite sides of said ring.

4. The device for suturing trocar sites as recited in claim 3 wherein said needles are pivotally affixed to said ring, said needles having a retracted position and an extended position.

5. The device for suturing trocar sites as recited in claim 4 wherein said needles are biased to said retracted position.

6. The device for suturing trocar sites as recited in claim 5 wherein said device is fabricated from stainless steel.

7. The device for suturing trocar sites as recited in claim 5 wherein said ring is fabricated from plastic.

* * * * *